United States Patent
Reuter et al.

(10) Patent No.: US 6,469,183 B1
(45) Date of Patent: Oct. 22, 2002

(54) METHOD OF PRODUCING PHTHALIC ACID ANHYDRIDE

(75) Inventors: Peter Reuter, Mannheim (DE); Guido Voit, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/856,292

(22) PCT Filed: Nov. 19, 1999

(86) PCT No.: PCT/EP99/08911

§ 371 (c)(1),
(2), (4) Date: May 21, 2001

(87) PCT Pub. No.: WO00/31013

PCT Pub. Date: Jun. 2, 2000

(30) Foreign Application Priority Data

Nov. 20, 1998 (DE) .......................... 198 53 675
Nov. 27, 1998 (DE) .......................... 198 54 892

(51) Int. Cl.[7] .............................. C07D 307/89
(52) U.S. Cl. ...................... 549/248; 549/249
(58) Field of Search ................ 549/248, 251, 549/249

(56) References Cited

U.S. PATENT DOCUMENTS

| | | | | |
|---|---|---|---|---|
| 2,574,512 A | | 11/1951 | Toland, Jr. ................ | 260/342 |
| 3,464,930 A | | 9/1969 | Friedrichsen et al. ....... | 252/469 |
| 3,509,179 A | | 4/1970 | Friedrichsen et al. ....... | 260/346 |
| 3,862,960 A | * | 1/1975 | Cheavens et al. | |

OTHER PUBLICATIONS

Nikolov et al. "Phthalic Anhydride from o–Xylene Catalysis: Science and Engineering" Catal. Rev. Sci. Eng., No. 33 (1991) pp. 319–374.

Glukhovskii et al. Chem Abs. vol. 100 No. 5 Jan., 1986.

* cited by examiner

*Primary Examiner*—Sreeni Padmanabhan
*Assistant Examiner*—Paul A. Zucker
(74) *Attorney, Agent, or Firm*—Keil & Weinkauf

(57) ABSTRACT

In a process for preparing phthalic anhydride by passing a gas stream comprising o-xylene, oxygen and sulfur dioxide at elevated temperature over a catalyst comprising heavy metals, the content of N-acyl compounds in the gas stream is restricted to less than 200 ppm, based on the weight of o-xylene.

12 Claims, No Drawings

METHOD OF PRODUCING PHTHALIC ACID ANHYDRIDE

This application is a 371 of PCT/EP99/08911 filed Nov. 19, 1999.

The present invention relates to a process for preparing phthalic anhydride by catalytic oxidation of o-xylene in the presence of sulfur dioxide in the gas phase.

Phthalic anhydride is produced industrially by catalytic oxidation of o-xylene in the gas phase. For this purpose, a gas stream comprising o-xylene and oxygen is passed at elevated temperature over a heterogeneous catalyst. The catalyst is generally located in a fixed-bed tube reactor. Particularly suitable catalysts for this process are supported catalysts which comprise an inert support and a catalytically active composition comprising, for example, the vanadium pentoxide and titanium dioxide applied thereto as a thin layer. Such catalysts are described, for example, in DE-A-1442590. The reactor tubes are generally surrounded by a salt melt in which a temperature of 350–420° C. is maintained. The vapors leaving the reactor are cooled and condensed.

It is known that catalytic amounts of sulfur dioxide can be added to the gas stream to increase the activity of the catalysts used, in particular after prolonged operation (see Nikolov et al., Catal. Rev.-Sci. Eng. 33 (1991) 319).

o-xylene is obtained industrially from a BTX fraction obtained by liquid extraction of suitable feedstocks, e.g. catalytic reforming products or hydrogenated pyrrolysis oils. As extractants, use is predominantly made of N-acyl compounds, in particular N-formylmorpholine. For this reason, the commercially available technical-grade o-xylene contains varying amounts of these N-acyl compounds.

When the process described at the outset for preparing phthalic anhydride is carried out industrially, it has been found that solid deposits are formed in the plant at points at which liquid or gaseous o-xylene comes into contact with an air stream containing sulfur dioxide at elevated temperature. These deposits are undesirable for various reasons, particularly because they lead to blockage of pipes, to densification of the catalyst bed or to thermal insulation of heat-exchange surfaces for the vaporization of liquid o-xylene.

It is an object of the present invention to develop the process described at the outset further so that the deposits described are avoided.

We have found that this object is achieved by a process for preparing phthalic anhydride by oxidation of technical-grade o-xylene in the gas phase, in which a gas stream comprising o-xylene, oxygen and sulfur dioxide is passed at elevated temperature over a catalyst comprising heavy metals, wherein the N-formylmorpholine content of the gas stream, preferably the total content of N-acyl compounds, is less than 200 ppm, preferably less than 50 ppm, in particular less than 10 ppm, based on the weight of o-xylene. The gas stream can, for example, contain from 5 to less than 200 ppm, from 5 to less than 50 ppm or from 5 to less than 10 ppm of N-acyl compounds, based on o-xylene.

Preferably, the gas stream comprises from 50 to 160 g, in particular 60–120 g, of o-xylene per m$^3$ and from 0.01 to 5% by weight, in particular from 0.1 to 1.5% by weight, based on o-xylene, of sulfur dioxide in a gas (mixture), in particular air, containing from 1 to 100% by volume, in particular from 2 to 50% by volume of oxygen.

For the purposes of the present invention, N-acyl compounds are low molecular weight nitrogen-containing organic compounds which bear an acyl group on the nitrogen atom. They can be open-chain amides or lactams. They generally have a molecular weight of less than 150, as a rule from 70 to 150. Typical representatives are, for example, N-methylpyrrolidone, N-formylmorpholine or N,N-dimethylformamide.

In the specifications given by the manufacturers of o-xylene, N-acyl compounds are usually not taken into account. Particular measures are therefore necessary to prevent the formation of the abovementioned deposits.

The content of N-acyl compounds in the gas stream is advantageously monitored by determining the content of N-acyl compounds in the technical-grade o-xylene prior to the reaction and
  a) if the content is less than 200 ppm based on o-xylene, using the technical-grade o-xylene for the reaction or
  b) if the content is greater than or equal to 200 ppm based on o-xylene, either
    i) rejecting the technical-grade o-xylene from the process or
    ii) adjusting the content of N-acyl compounds in the technical-grade o-xylene to less than 200 ppm, based on o-xylene, and using the technical-grade o-xylene obtained in this way for the reaction.

The content of N-acyl compounds can be determined, for example, by means of gas chromatography, if desired with the aid of suitable reference substances. Suitable methods of setting a low content of N-acyl compounds are, for example, distillation processes.

Catalysts suitable for the process of the present invention are those which are customarily used for the air oxidation of o-xylene. These are, in general, catalysts based on the vanadium pentoxide. The vanadium catalysts can be doped with various other elements of the Periodic Table, e.g. with cesium (see WO 98/37965), phosphorus (DE-A 1769998) or with rubidium and/or cesium (DE-C 2436009 and DE-C 2547624). The catalysts are generally used on supports. The support has, for example, the shape of a sphere or preferably a ring shape. It comprises, for example, sintered or fused silicates, porcelain, alumina, silicon carbide or silica. The catalytically active composition, which coats the support in a thickness of preferably 0.05–1 mm, comprises, for example, 1–30% by weight of vanadium pentoxide and 70–99% by weight of titanium dioxide. It may, if desired, further comprise small amounts, e.g. up to 5% by weight, based on the catalytic composition, of antimony, zirconium or tin, phosphorus, rubidium or cesium, e.g. in the form of their oxides. The active composition makes up about 3–50% by weight of the finished supported catalyst. The catalyst is generally installed in a plurality of tubes in a multitube reactor.

The process of the present invention is advantageously carried out as follows: The preferably dust-free, filtered air is compressed in a compressor. This compressed air is heated in an air preheater, for example by means of steam. o-Xylene is subsequently injected into this hot air stream. The injected o-xylene vaporizes and disperses in the air stream. The loading of o-xylene per cubic meter of air can be variable. It can lie below the explosive limit (44 g/m$^3$). However, loadings of, for example, 44–100 g of o-xylene per m$^3$ of air are also possible. This gas mixture, into which a catalytic amount of $SO_2$, usually from 0.1 to 1.5% by weight based on o-xylene, is metered, is passed into the reactor at the top. It is distributed over the tubes of the multitube reactor and flows over the catalyst. The resulting heat of reaction is removed via a molten salt bath, e.g. comprising a mixture of potassium nitrate and sodium nitrite, as heat transfer medium. The salt bath is generally thermostated to from 300 to 450° C. The hot salt can be cooled, for example, by generation of high-pressure steam. The gas-phase oxidation is advantageously carried out with two or more zones, preferably two zones, of the catalyst bed present in the reaction tube being thermostated to different reaction temperatures. It is here possible to use, for example, reactors having separate salt baths, as are described, for example, in DE-A 2201525 or DE-A 2830765. It is possible, as described in DE-A 4013051, for the reaction zone nearest the inlet point of the gas stream, which zone generally makes up from 25 to 75% by volume of the total catalyst volume, to be thermostated to a reaction temperature which is from 1 to 20° C., preferably from 1 to 10° C. and in particular from 2 to 80° C., higher than that in the reaction zone nearest the gas outlet.

The phthalic anhydride formed is preferably deposited from the product gases in solid form by desublimation. Alternately operating melt condensers are particularly suitable for this purpose. Here, the cooled product gas is passed into a group of condensers. Each one of these condensers operates in a heating and cooling or melting and loading cycle. When one condenser is in the loading phase, phthalic anhydride desublimes on the cooling surfaces. A cooled heat transfer medium flows through the cooling surfaces. When a particular pressure drop is encountered in the condenser or after a predetermined time, the condenser is then switched from the product gas stream. The cold heat transfer medium is displaced by hot heat transfer medium and the crude anhydride is thus melted from the cooling surface and collected. The crude phthalic anhydride can subsequently be subjected to a distillation.

The process of the present invention is particularly advantageous when using technical-grade o-xylene which has been obtained by extraction or extractive distillation of a mixture comprising aromatic compounds with the aid of N-acyl compounds. To isolate aromatics such as o-xylene from crude BTX streams, use is usually made of extraction and extractive distillation processes. Extractive distillation differs from a normal distillation in that it is carried out in the presence of a high-boiling solvent which has a high solvent capability for aromatic compounds and a low solvent capability for paraffins and naphthalenes. This solvent customarily comprises N-acyl compounds. The solvent is advantageously introduced in the vicinity of the top of the distillation column and above the point at which the BTX stream is fed in. The nonaromatic compounds are generally distilled off at the top of the column and the aromatics-rich solvent is taken off as bottom product. The aromatic compounds can then be distilled or stripped from the solvent in a second column and the solvent can be recirculated. Separation of the various aromatic compounds is advantageously carried out in subsequent distillation steps. The ratios of solvent to BTX stream are generally in the order of from 2:1 to 6:1.

In liquid-liquid extraction, aromatic compounds are extracted from nonaromatic material using a polar solvent, e.g. N-acyl compounds, having a high selectivity for the former. The solvent is generally introduced at the top of the extraction vessel. Various configurations of extractor are possible, including packed columns, sieve tray arrangements and the like. The crude BTX fraction is advantageously fed in at about the middle of the extractor. The nonaromatic raffinate can then be taken off at the top of the reactor while the aromatics-rich solvent is taken off at the bottom and can be passed to a distillation column in which the aromatics are taken off at the top. The solvent which has been freed of aromatics can be returned to the extractor. The aromatics stream taken off at the top is advantageously distilled to separate the individual aromatic components.

The process of the present invention is illustrated by the following examples:

EXAMPLE

Over a number of months, 8400 kg of o-xylene/h were vaporized at 210° C. and a pressure of 1.4 bar in an air stream of 93000 m$^3$/h mixed with 25 kg/h of gaseous $SO_2$. The o-xylene had a nitrogen content of about 1 ppm. The vaporizer section displayed no deposits after this period of time.

Comparative Example 1

This was carried out as described in Example 1, but the o-xylene had an N-formylmorpholine content of 200 ppm. After operating the vaporizer for two weeks, about 20 kg of residue had to be removed from the vaporizer section. This residue typically had the following elemental composition: 54% C, 22% O, 10% N, 10% S, 4% H.

Comparative Example 2

This was carried out as described in Comparative Example 1, but the air stream was free of $SO_2$. No deposits were found.

We claim:

1. A process for preparing phthalic anhydride by oxidation of o-xylene in the gas phase, which comprises i) providing a technical-grade o-xylene which comprises one or more N-acyl compounds,
   ii) determining the content of N-acyl compounds in the technical-grade o-xylene, and
      a) passing the technical-grade o-xylene to stage (iii) if the content of N-acyl compounds is less than 200 ppm based on o-xylene, or
      b) if the content is greater than or equal to 200 ppm based on o-xylene, either $b_1$) rejecting the technical-grade o-xylene from the process, or $b_2$) adjusting the content of N-acyl compounds in the technical-grade o-xylene to less than 200 ppm, based on o-xylene, and passing the resulting technical-grade o-xylene to stage (iii), and
   iii) preparing a gas stream comprising the technical-grade o-xylene which has a content of N-acyl compounds of less than 200 ppm based on o-xylene, oxygen and sulfur dioxide, and passing the gas stream at elevated temperature over a catalyst comprising heavy metals.

2. The process of claim 1, wherein the content of N-acyl compounds is adjusted by distillation.

3. The process of claim 1, wherein the content of N-acyl compounds in the technical-grade o-xylene admitted to stage (iii) is less than 50 ppm.

4. The process of claim 1, wherein the technical-grade o-xylene provided in stage (i) is one which has been obtained by extraction or extractive distillation of a mixture comprising aromatic compounds with the aid of one or more N-acyl compounds.

5. The process of claim 1, wherein the o-xylene provided in stage (i) comprises one or more N-acyl compounds selected from the group consisting of N-formylmorpholine, N-methylpyrrolidone and N,N-dimethylformamide.

6. A process for preparing phthalic anhydride by oxidation of o-xylene in the gas phase, which comprises i) providing a technical-grade o-xylene which comprises N-formylmorpholine,
ii) determining the content of N-N-formylmorpholine in the technical-grade o-xylene, and
   a) passing the technical-grade o-xylene to stage (iii) if the content of N-formylmorpholine is less than 200 ppm based on o-xylene, or
   b) if the content is greater than or equal to 200 ppm based on o-xylene, either $b_1$) rejecting the technical-grade o-xylene from the process, or $b_2$) adjusting the content of N-formylmorpholine in the technical-grade o-xylene to less than 200 ppm, based on o-xylene, and passing the resulting technical-grade o-xylene to stage (iii), and
iii) preparing a gas stream comprising the technical-grade o-xylene which has a content of N-formylmorpholine of less than 200 ppm based on o-xylene, oxygen and sulfur dioxide, and passing the gas stream at elevated temperature over a catalyst comprising heavy metals.

7. The process of claim 5, wherein the content of N-acyl compounds is adjusted by distillation.

8. The process of claim 5, wherein the content of N-acyl compounds in the technical-grade o-xylene admitted to stage (iii) is less than 50 ppm.

9. The process of claim 5, wherein the technical-grade o-xylene provided in stage (i) is one which has been obtained by extraction or extractive distillation of a mixture comprising aromatic compounds with the aid of the one or more N-acyl compounds.

10. The process of claim 6, wherein the content of N-formylmorpholine is adjusted by distillation.

11. The process of claim 6, wherein the content of N-formylmorpholine in the technical-grade o-xylene admitted to stage (iii) is less than 50 ppm.

12. The process of claim 6, wherein the technical-grade o-xylene provided in stage (i) is one which has been obtained by extraction or extractive distillation of a mixture comprising aromatic compounds with the aid of N-formylmorpholine.

* * * * *